United States Patent [19]

Cook et al.

[11] Patent Number: 4,689,200
[45] Date of Patent: Aug. 25, 1987

[54] SYSTEMS INHIBITED AGAINST CORROSION AND/OR SCALE DEPOSITION

[75] Inventors: Barry Cook; Norman Richardson; Joseph Tames, all of Manchester, England

[73] Assignee: Ciba-Geigy Corporation, Ardsley, N.Y.

[21] Appl. No.: 838,890

[22] Filed: Mar. 11, 1986

Related U.S. Application Data

[63] Continuation of Ser. No. 694,480, Jan. 23, 1985, abandoned, which is a continuation of Ser. No. 614,375, May 24, 1984, abandoned, which is a continuation of Ser. No. 414,178, Sep. 2, 1982, abandoned.

[30] Foreign Application Priority Data

Sep. 4, 1981 [GB] United Kingdom ............... 8126809
Jun. 11, 1982 [GB] United Kingdom ............... 8217052

[51] Int. Cl.$^4$ ........................... C23F 11/16; C02F 5/14
[52] U.S. Cl. .................................... 422/15; 106/14.12; 106/14.13; 106/14.14; 106/18.31; 210/699; 252/49.3; 252/180; 252/181; 252/389.2; 252/396; 422/17
[58] Field of Search ............... 252/49.3, 180, 389.2, 252/396, 181; 106/14.12, 14.13, 14.14, 18.31; 210/699; 422/15, 17

[56] References Cited

U.S. PATENT DOCUMENTS

| 3,032,500 | 5/1962 | Milks et al. | 252/8.55 |
| 3,719,598 | 3/1973 | King | 252/49.3 |
| 3,933,427 | 1/1976 | Bohnsack et al. | 21/2.7 A |
| 4,042,324 | 8/1977 | Auel et al. | 21/2.7 A |
| 4,057,511 | 11/1977 | Bohnsack et al. | 252/389 A |
| 4,105,551 | 8/1978 | Smith et al. | 252/180 |
| 4,243,417 | 1/1981 | Grourke et al. | 106/14.13 |

FOREIGN PATENT DOCUMENTS

| 1045373 | 12/1958 | Fed. Rep. of Germany . |
| 2310450 | 9/1974 | Fed. Rep. of Germany . |
| 2632774 | 2/1977 | Fed. Rep. of Germany . |
| 55-2718A | 1/1980 | Japan . |
| 1017115 | 2/1980 | Japan . |

Primary Examiner—Robert A. Wax
Attorney, Agent, or Firm—Harry Falber

[57] ABSTRACT

Aqueous or partly aqueous systems are treated against the corrosion of metals, especially ferrous metals, in contact therewith, and/or against scale deposition therefrom, by adding to these systems from 0.1 to 50 000 ppm of 2-hydroxyphosphonoacetic acid having the formula I

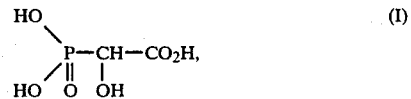

or a water-soluble salt thereof.

7 Claims, No Drawings

SYSTEMS INHIBITED AGAINST CORROSION AND/OR SCALE DEPOSITION

This application is a continuation of application Ser. No. 694,480, filed Jan. 23, 1985, which is a continuation of application Ser. No. 614,375, filed May 24, 1984, which in turn is a continuation of application Ser. No. 414,178, filed on Sept. 2, 1982, all now abandoned.

The present invention relates to aqueous or partly aqueous systems, especially to aqueous systems inhibited against corrosion of metals in contact therewith, and/or inhibited against scale deposition therefrom.

In German Offenlegungsschrift No. 2310450, there are described compounds of formula:

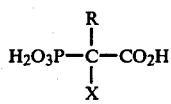

wherein R is an alkyl residue having 1 to 4 carbon atoms and X is hydrogen or a hydroxyl group. These compounds and their water-soluble salts are said to be useful as complexing agents for polyvalent metal ions. The compounds are also said to be suitable for use as corrosion—or scale—inhibitors for cooling water.

In German Offenlegungsschrift No. 2310450, earlier prior art is discussed, and distinguished over, in the following terms. German Patent Specification No. 1045373 is cited and is said to disclose the use of methylene diphosphonic acid as a good complexing agent for calcium.

It is stated that, if one phosphonic acid group is replaced by a carboxylic acid group, then undesirable eutrophic (biological nutrient) properties are reduced, but the complexing properties of the resulting phosphonoacetic acid are also substantially reduced. In order to combine good complexing properties with reduced eutrophic properties, Offenlegungsschrift No. 2310450 teaches that one of the protons of the methylene group of the phosphonoacetic acid must be replaced by a $C_{1-4}$-alkyl group; the second proton may optionally be replaced by a hydroxyl group.

In clear contradistinction to this prior teaching, we have now found, surprisingly, that much improved metal corrosion inhibition and/or scale deposition inhibition, is attained in aqueous systems by the incorporation of 2-hydroxyphosphonoacetic acid as opposed to the use of 2-hydroxy-2-phosphonopropionic acid. Moreover, 2-hydroxyphosphonoacetic acid exhibits excellent corrosion inhibition in systems which are only partly aqueous e.g. aqueous machining fluids, antifreeze fluids, water/glycol hydraulic fluids and aqueous surface coatings such as water-based emulsion paints and aqueous powder coatings for metals.

The present invention provides an aqueous or partly aqueous system inhibited against corrosion of metals, especially ferrous metals, in contact therewith, and/or inhibited against scale deposition therefrom, comprising adding to this system from 0.1 to 50.000 ppm of 2-hydroxyphosphonoacetic acid having the formula I

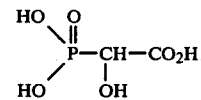

or a water-soluble salt thereof.

2-Hydroxyphosphonoacetic acid is a known compound having been described in U.S. Pat. No. 3,032,500 and, more recently in European Patent Application No. 0050792. It can be prepared by known methods e.g. by reacting orthophosphorous acid, a salt or a solution thereof, or phosphorus trichloride, with glyoxylic acid, a salt or a solution thereof.

2-Hydroxyphosphonoacetic acid may be used as the free acid or as a water-soluble salt or partial salt of e.g. an alkali metal, an alkaline earth metal, ammonia or an alkylamine (optionally substituted with one to six hydroxyl groups) and containing 1 to 20, preferably 1 to 12 carbon atoms.

Examples of suitable salts are those of:

Lithium, sodium, potassium, calcium, strontium, magnesium, ammonia, methylamine, ethylamine, n-propyl-amine, trimethylamine, triethylamine, n-butylamine, n-hexylamine, octylamine, ethanolamine, diethanolamine, triethanolamine or morpholine.

0.1 to 50.000 ppm of 2-hydroxyphosphonoacetic acid is added to aqueous systems in order to inhibit metal corrosion and/or deposition of scale from the system.

In practice, the amount of 2-hydroxyphosphonoacetic acid which is added to the aqueous system to be treated, will vary depending upon the function which 2-hydroxyphosphonoacetic acid is required to perform. For corrosion-inhibiting protective treatments, optionally in combination with scale inhibiting treatments, the amount of 2-hydroxyphosphonoacetic acid added to the aqueous system is conveniently within the range of from 0.1 to 50.000 ppm (or 0.00001 to 5% by weight), preferably from 1 to 500 ppm (or 0.0001 to 0.05% by weight), based on the aqueous system. For solely anti-scale purposes, the amount of 2-hydroxyphosphonoacetic acid used is conveniently from 1 to 200 ppm, preferably 1 to 30 ppm, based on the aqueous system.

With respect to aqueous systems which may be treated according to the present invention, of particular interest with respect to combined corrosion inhibition and anti-scale treatments are cooling water systems, steam generating systems, sea-water evaporators, hydrostatic cookers, gas scrubbing systems and closed circuit heating systems; for corrosion inhibition treatments alone, aqueous systems of particular interest include aqueous machining fluid formulations (e.g. for use in boring milling, reaming, broaching, drawing, turning, cutting, sawing, grinding, and thread-cutting operations or in non-cutting shaping in spinning, drawing or rolling operations), aqueous scouring systems, aqueous glycol antifreeze systems, water/glycol hydraulic fluids; and aqueous based polymer surface-coating systems.

The compound of formula I may be used alone or in conjunction with other compounds known to be useful in the treatment of aqueous systems.

In the treatment of systems which are completely aqueous, such as cooling water systems, steam-generating systems, sea-water evaporator systems, hydrostatic cookers, and closed circuit heating systems, further corrosion inhibitors may be used such as, for example, water soluble zinc salts; phosphates; polyphosphates; phosphonic acids and their salts, for example, acetodiphosphonic acid, nitrilotrismethylene phosphonic acid and methylamino dimethylene phosphonic acid; other phosphonocarboxylic acids and their salts, for example, those described in German Offenlegungsschrift No. 2632774, 2-phosphonobutane-1,2,4-tricarboxylic acid and those disclosed in GB No. 1572406; chromates for example, sodium chromate; nitrates, for example sodium nitrate; nitrites e.g. sodium nitrite; benzotriazole, bis-benzotriazole or copper deactivating benzotriazole or tolyltriazole derivatives; N-acyl sarcosines; N-acylimino diacetic acids; ethanolamines; fatty amines; and polycarboxylic acids, for example, polymaleic acid and polyacrylic acid, as well as their respective alkali metal salts, copolymers of maleic anhydride, copolymers of acrylic acid, and substituted derivatives of polymaleic and polyacrylic acids and their copolymers.

Moreover, in such completely aqueous systems, the compound of formula I may be used in conjunction with further dispersing and/or threshold agents, e.g. polymerised acrylic acid (or its salts), phosphinopolycarboxylic acids (as described and claimed in British Pat. No. 1458235), hydrolysed polyacrylonitrile, polymerised methacrylic acid and its salts, polyacrylamide and copolymers thereof from acrylic and methacrylic acids, lignin sulphonic acid and its salts, tannin, naphthalene sulphonic acid/formaldehyde condensation products, starch and its derivatives, and cellulose. Specific threshold agents, such as for example, 2-phosphonobutane-1,2,4-tricarboxylic acid, acetodiphosphonic acid, hydrolysed polymaleic anhydride and its salts, alkyl phosphonic acids, 1-aminoalkyl-1,1-diphosphonic acids and their salts, and alkali metal polyphosphates, may also be used.

Precipitating agents such as alkali metal orthophosphates, carbonates; oxygen scavengers such as alkali metal sulphites and hydrazines; sequestering agents such as nitrilotriacetic acid and its salts; antifoaming agents such as silicones e.g. polydimethylsiloxanes, distearylsebacamide, distearyl adipamide and related products derived from ethylene oxide and/or propylene oxide condensations, in addition to fatty alcohols, such as capryl acohols and their ethylene oxide condensates; and biocides e.g. amines, quaternary ammonium compounds, chlorophenols, sulphur-containing compounds such as sulphones, methylene bis thiocyanates and carbamates, isothiazolones, brominated propionamides, triazines, phosphonium compounds, chlorine and chlorine-release agents and organometallic compounds such as tributyl tin oxide.

If the system to be treated according to the invention is not completely aqueous e.g. an aqueous machining fluid formulation, it may be e.g. a water dilutable cutting or grinding fluid.

The aqueous machining fluid formulations of the invention may be e.g. metal working formulations. By "metal working" we mean "reaming, broaching, drawing, spinning, cutting, grinding, boring, milling, turning, sawing, non-cutting shaping or rolling". Examples of water-dilutable cutting or grinding fluids into which the corrosion inhibiting compound of Formula I may be incorporated include:

(a) Aqueous concentrates of one or more corrosion inhibitors, and optionally one or more anti-wear additives, used at dilutions of 1:50 to 1:100, which are usually employed as grinding fluids;

(b) Polyglycols containing biocides, corrosion inhibitors and anti-wear additives which are used at dilutions of 1:20 to 1:40 for cutting operations and 1:60 to 1:80 for grinding;

(c) Semi-synthetic cutting fluids similar to (b) but containing in addition 10 to 25% oil with sufficient emulsifier to render the water diluted product translucent;

(d) An emulsifiable mineral oil concentrate containing, for example, emulsifiers, corrosion inhibitors, extreme pressure/anti-wear additives, biocides, antifoaming agents, coupling agents etc; they are generally diluted from 1:10 to 1:50 with water to a white opaque emulsion;

(e) A product similar to (d) containing less oil and more emulsifier which on dilution to the range 1:50 to 1:100 gives a translucent emulsion for cutting or grinding operations.

Mixtures of sodium nitrite and triethanolamine have been used to inhibit corrosion in metal working but because of related toxicity problems, due e.g. to the danger of forming N-nitrosamines, and because of legal regulations in some countries relating to effluents, alternatives to the use of sodium nitrite are being sought.

For those partly-aqueous systems in which the aqueous system component is an aqueous machining fluid formulation the compound of formula I may be used singly, or in admixture with other additives e.g. known further corrosion inhibitors and/or extreme-pressure additives.

Examples of other corrosion inhibitors which may be used in these aqueous systems, in addition to the compound of formula I, include the following groups:

(a) Organic acids, their esters or ammonium, amine, alkanolamine and metal salts, for example, benzoic acid, p-tert-butyl benzoic acid, disodium sebacate, triethanolamine laurate, iso-nonanoic acid, triethanolamine salt of (p-toluene sulphonamido caproic acid), sodium N-lauroyl sarcosinate or nonyl phenoxy acetic acid;

(b) Nitrogen containing materials such as the following types: fatty acid alkanolamides; imidazolines, for example, 1-hydroxyethyl-2-oleyl-imidazolines; oxazolines; triazoles, for example, benzotriazoles; triethanolamines; fatty amines; and inorganic salts, for example, sodium nitrate;

(c) Phosphorus containing materials such as the following types: amine phosphates, phosphonic acids or inorganic salts, for example, sodium dihydrogen phosphate or zinc phosphate;

(d) Sulphur containing compounds such as the following types: sodium, calcium or barium petroleum sulphonates, or heterocyclics, for example, sodium mercaptobenzothiazole.

Nitrogen containing materials, particularly triethanolamine, are preferred.

Examples of extreme pressure additives which may be present in the systems of the present invention include sulphur and/or phosphorus and/or halogen containing materials, for instance, sulphurised sperm oil, sulphurised fats, tritolyl phosphate, chlorinated paraffins or ethoxylated phosphate esters.

When triethanolamine is present in the aqueous systems treated according to the present invention, it is preferably present in an amount such that the ratio of compound of formula I to triethanolamine is from 2:1 to 1:20.

The partly-aqueous systems treated by the method of the present invention may also be aqueous surface-coating compositions e.g. primer emulsion paints and aqueous powder coatings for metallic substrates.

The aqueous surface-coating composition may be e.g. a paint such as styrene-acrylic copolymer emulsion paint, a resin, latex, or other aqueous based polymer surface-coating systems.

Sodium nitrite and sodium benzoate have been used to inhibit flash rusting of aqueous based primer paints but because of related toxicity problems and problems of emulsion stability at the high ionic concentrations used, industry is moving away from sodium nitrite and sodium benzoate.

In aqueous surface-coating compositions treated according to the invention the compound of formula I may be used singly, or in admixture with other additives e.g. known corrosion inhibitors, biocides, emulsifiers and/or pigments.

The further known corrosion inhibitors which may be used are e.g. those of classes (a), (b), (c) and (d) hereinbefore defined.

Examples of biocides which may be used in these aqueous systems, in addition to the compound of formula I, include the following:

Phenols, and alkyl- and halogenated phenols, for example pentachlorophenol, o-phenyl phenol, o-phenoxyphenol and chlorinated o-phenoxyphenol, and salicylanilides, diamines, triazines and organometallic compounds such as organomercury compounds and organotin compounds.

Examples of pigments which may be used in these aqueous systems, in addition to the compound of formula I, include titanium dioxide, zinc chromate, iron oxide and organic pigments such as the phthalocyanines.

The following Examples further illustrate the present invention. Parts and percentages shown therein are by weight.

The 2-hydroxyphosphonoacetic acid active ingredient used in the following use Examples 2 to 6 was prepared as follows:

EXAMPLE 1

(A) 16.3 parts (0.11 mole) 50% aqueous glyoxylic acid and 8.2 parts (0.1 mole) orthophosphorous acid are heated together with stirring at 98°–100° for 24 hours to give 24.5 parts of 60% aqueous 2-hydroxyphosphonoacetic acid.

(B) 150 parts of 60% aqueous solution of 2-hydroxyphosphonoacetic acid obtained according to Example 1A is evaporated under reduced pressure (20 millibars) to give 104 parts of a viscous brown oil. Then this oil is induced to crystallise. The crude crystalline mass is then triturated with acetone to remove impurities. The resulting buff coloured crystalline 2-hydroxyphosphonoacetic acid is removed by filtration, washed with acetone, and dried.

The crude crystalline 2hydroxyphosphonoacetic acid so obtained is then recrystallized from water to give pure 2-hydroxyphosphonoacetic acid as white crystals m.p. 165°–167.5° C.

$^{31}$P-NMR $\delta = -14$ ppm (relative to external $H_3PO_4$);
H-NMR P–C$\underline{H}$ $\delta = 4.24$ ppm,
IR COOH: 1745 cm$^{-1}$, P=O: 1200 cm$^{-1}$.

EXAMPLE 2

Corrosion inhibitor activity of the active compound of formula I is demonstrated in the following way by the Aerated Solution Bottle Test and using a standard corrosive water made up as follows:
20 g.: $CaSO_4.2H_2O$
15 g.: $MgSO_4.7H_2O$
4.6 g.: $NaHCO_3$
7.7 g.: $CaCl_2.6H_2O$
Distilled water 205 liters.

Mild steel coupons, 5 cms.×2.5 cms. are scrubbed with pumice, immersed for one minute in hydrochloric acid and then rinsed, dried and weighed.

The desired proportion of additive combination is dissolved in 200 ml. of standard corrosive water. Two steel coupons are suspended in the solution, and the whole is stored in a closed bottle in a thermostat at 40° C. During the storage period, air is passed into the solution at 500 ml/minute, the passage of the air being screened from the steel coupon; any water losses by evaporation are replaced with distilled water.

After 64 hours, the steel coupons are removed, scrubbed without pumice, immersed for one minute in hydrochloric acid inhibited with 1% by weight of hexamine and then rinsed, dried and reweighed. A certain loss in weight will have occurred. A blank test i.e. immersion of mild steel specimens in the test water in the absence of any potential corrosion inhibitor, is carried out with each series of tests. The corrosion rates are calculated in milligrams of weight loss/q. decimeter/day (m.d.d.) but for convenience the results are shown as percentage protection, which is defined as follows:

% Protection =

$$\frac{\text{Corrosion rate for blank (in } m.d.d.) - \text{corrosion rate for sample (in } m.d.d.)}{\text{Corrosion rate for blank (in } m.d.d.)} \times 100$$

The results obtained in a series of tests using 100 ppm, 90 ppm, 80 ppm, 70 ppm, 60 ppm, 50 ppm and 40 ppm respectively, of hydroxyphosphonoacetic acid, as produced in Example 1 (A) are set out in Table 1.

TABLE 1

| | Mild Steel Corrosion Inhibition of hydroxyphosphonoacetic acid in a Standard Corrosive Water | | | | | | |
|---|---|---|---|---|---|---|---|
| Example | Structure | % Corrosion Inhibition | | | | | |
| | | 100 ppm | 90 ppm | 80 ppm | 70 ppm | 60 ppm | 50 ppm | 40 ppm |
| 2 | $\begin{array}{c} O \\ \parallel \\ (HO)_2PCH-CO_2H \\ \mid \\ OH \end{array}$ ex. Example 1(A) | 100 | 100 | 100 | 100 | 100 | 99 | 97.5 |

The results in Table 1 show the effective mild steel corrosion inhibitory properties of hydroxyphosphonoacetic acid.

EXAMPLE 3

The corrosion resistance of an aqueous cutting fluid composition of the invention is assessed by the following procedure, which is a modification of the Institute of Petroleum Test 287.

A 1% aqueous solution of the compound under test is prepared containing sufficient triethanolamine (TEA) to bring its pH value to 9.

This solution is further diluted by factors of 2, 4, 8 and 16 and each of these solutions contacted with cast iron chips according to the method set forth in the IP 287 Test Procedure. The test is carried out using deionised water and IP 287 hard water.

The visual assessment of the condition of the metal chips after exposure is in accordance with the following guidelines.

| Degree of rusting | Rating |
|---|---|
| no rusting | 0 |
| ≦5 small specks | T (trace) |

The results obtained are set out in Table 2, and show the corrosion-inhibiting activity of the compounds of formula I in an aqueous fluid composition.

TABLE 2

Cast Iron Inhibition in Aqueous Cutting Fluids

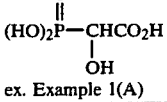

| Example | Structure | % TEA for 1% of the Compound of Example | pH | Dilution* Ratio | % | Rust (deionised water) | Rust (hard water) |
|---|---|---|---|---|---|---|---|
| 2 | (HO)$_2$P(=O)—CH(OH)CO$_2$H ex. Example 1(A) | 12.5 | 9.0 | 1:15 | 0.5 | O | O |
| | | | | 1:30 | 0.25 | O | O |
| | | | | 1:60 | 0.125 | O | T |
| | | | | 1.120 | 0.062 | T | T |

*"Dilution Ratio" is the ratio of triethanolamine + compound to water
"Dilution %" is the percentage concentration of the compound only.

EXAMPLE 4

The effectiveness of the compound of formula I in inhibiting flash rusting is demonstrated in the following way.

A typical primer styrene-acrylic copolymer emulsion paint is prepared to the followng formulation using a high speed stirrer, all parts being by weight

| | |
|---|---|
| Zinc orthophosphate | 190 parts |
| Titanium dioxide RCR-2 | 58 parts |
| Modocol ® EK-600 (4% in water) (a polyacrylate) | 64 parts |
| Vinapol ® 1640 (5% in water) (Potassium polymethacrylate-Vinyl Products Ltd.) | 36 parts |
| Ammonia (0.880) | 10 parts |
| Water | 92 parts |
| Vinacryl ® M 175 (Styrene/acrylic copolymer-Vinyl Products Ltd.) | 549 parts |
| Acticide ® MPM (Organo-mercury compound-Thor Chemicals Ltd.) | 1 part |
| | 1000 parts |

An aqueous mixture of the compound of formula I as obtained in Example 1(A) and triethanolamine (TEA) (Compound of formula 1:TEA:WATER, 3:48:2 by weight) is incorporated, with stirring into 100 g aliquots of this primer to give a concentration of 500, 250 and 100 ppm of the compound of formula 1. A control, without corrosion inhibitor is included for reference.

Paint samples are applied by brush to duplicate steel panels (15.24 cm×10.16 cm (which had been freshly blast-cleaned to Sa 3. One coat is applied over the face of the panels and, when dry, a second coat is then applied over half the panel (brushing out at right angles to the direction of brushing of the first coat). The painted panels are allowed to dry in a controlled environment (20° C., 60% RH) and a visual assessment of flash rusting is then made.

The flash rusting is evaluated visually and according to the number and nature of the rust specks given a numerical rating on a scale from 0 to 5; 0=no flash rusting, 5=severe flash rusting.

The results obtained are set out in Table 3.

TABLE 3

Steel Corrosion Inhibition in styrene-acrylic Copolymer Emulsion Paint

| Panel | Inhibitor | Level of Inhibitor Incorporation (ppm) | Rating 1st Coat |
|---|---|---|---|
| 1 | | 2000 | 0 |
| 2 | | 2000 | 0 |
| 3 | Compound of formula I | 500 | 0/1 |
| 4 | | 500 | 0/1 |
| 5 | | 250 | 0/1 |
| 6 | | 250 | 0/1 |
| 7 | | 100 | 2/3 |
| 8 | | 100 | 2/3 |
| 9 | No inhibitor | — | 4 |
| 10 | | — | 4 |

The results in Table 3 show the superior corrosion inhibition of emulsion paint containing 2-hydroxyphosphonoacetic acid, relative to a control paint.

EXAMPLES 5 AND 6

Threshold Test for Calcium Carbonate

The following solutions (a), (b) and (c) are prepared:
(a) Calcium nitrate solution 1.470 grams of calcium nitrate tetrahydrate are dissolved in deionised water and the solution is made up to 1 liter;

(b) Sodium carbonate solution 0.646 gram of sodium carbonate is dissolved in deionised water and the solution is made up to 1 liter.

(c) Solution of 2-hydroxy-phosphonoacetic acid 2-hydroxy-phosphonoacetic acid as obtained in either Example 1 (A) or 1 (B) is dissolved in water to give a solution containing 1000 ppm of active ingredient.

50 mls. of the calcium nitrate solution are placed in a 120 g. glass bottle fitted with a screw cap. To this solution is added that volume of solution (c) required to produce a concentration of 2-hydroxy-phosphonoacetic acid of 5 ppm, 7.5 ppm 10 ppm, respectively, in the final volume (100 ml) of test solution (e.g. 1.0 ml of 0.1% of solution (c) produce a concentration of 10 ppm of 2-hydroxy-phosphonoacetic acid in the test solution). 50 ml of solution (b) are added and the mixture is shaken. The test solution is stored in a constant temperature bath, maintained at 25° C. for 24 hours. 25 mls. of the test solution are withdrawn, a crystal of Patton and Reader's Reagent [2-hydroxy-1-(2'-hydroxy-4'-sulpho-1'-naphthylazo)-3-naphthoic acid] is added, followed by two pellets of sodium hydroxide. The resulting solution is titrated with a standard 0.01M solution of ethylenediamine tetra-acetic acid di-sodium salt.

The results, as set out in the following Table 4, are expressed as % inhibition of precipitation of calcium carbonate relative to a blank titre (i.e. one containing no 2-hydroxyphosphonoacetic acid).

$$\% \text{ inhibition} = \frac{(\text{Titre} - \text{blank titre})}{(7.78 - \text{blank titre})} \times 100$$

7.78 is the maximum possible titration for 100% inhibition.

TABLE 4

| Example | Inhibitor Structure | % Inhibition of precipitation at additive level of | | |
|---------|---------------------|---------|----------|---------|
| | | 5 ppm | 7.5 ppm | 10 ppm |
| 5 | $H_2O_3PCHCO_2H$<br>$\|$<br>$OH$<br>ex. Example 1(A) | 92.0 | 93.5 | 96.5 |
| 6 | $H_2O_3PCHCO_2H$<br>$\|$<br>$OH$<br>ex. Example 1(B) | 89.4 | 95.2 | 95.9 |

EXAMPLE 7

The combined scale and corrosion inhibition properties of the invention are assessed by the following procedure in evaporative cooling water rigs.

The standard method of operation of a rig is to concentrate the water to the desired degree. Once concentrated, the pre-weighed corrosion coupons and heat exchanger are put into the rig and the inhibitor added. A passivation dose of scale/corrosion inhibitor is added in the feedwater for a period of three days, after which the levels of inhibitor are allowed to fall to the maintenance dose level over a period of 2 days. Once the inhibitor dose level is at the desired maintenance level, sufficient scale/corrosion inhibitor is added in the feedwater to maintain that level for 10 days. After this time, the corrosion rates are calculated by the weight loss of the metal coupons, and the scaling rate determined by the weight gain of the heat exchanger.

Standard operation parameters for the evaporative cooling water rigs:
System volume: 20 liters
Flow rate: 15 liters/min
Flow velocity: 0.3 meters/second
System temperature: 40° C.
ΔT across heat exchanger: 2° C.
Half life approx.: 30 hours. Typical analysis of water used.

| pH | 8.9 | | |
|----|-----|----|----|
| pA* | 120 | ppm | (as $CaCO_3$) |
| TA* | 470 | ppm | (as $CaCO_3$) |
| TH* | 450 | ppm | (as $CaCO_3$) |
| Cl | 75 | ppm | (as $Cl^-$) |

| Example | Inhibitor Structure | Active Dose (ppm) | Time (days) | Scaling rate grams/day | Mild steel corrosion rate MDD |
|---------|---------------------|-------------------|-------------|------------------------|-------------------------------|
| — | Control | — | — | 2.85 | 32.5 |
| 7 | $H_2O_3PCHCO_2H$<br>$\|$<br>$OH$<br>ex. Example 1(A) | 75<br>15 | 3<br>10 | 0.15 | 6.1 |

*pA denotes "phenol alkalinity"
TA denotes "total alkalinity" and
TH denotes "total hardness"

What is claimed is:

1. A method of inhibiting scale formation on and corrosion of metal surfaces, comprising contacting said surfaces with a scale forming or corrosive medium which contains 5 to 5000 ppm of 2-hydroxyphosphonoacetic acid, or a salt thereof which is soluble in the medium.

2. The method according to claim 1, wherein 5 to 500 ppm of 2-hydroxyphosphonoacetic acid or a salt thereof is present in said medium.

3. The method according to claim 2, wherein 5 to 200 ppm of 2-hydroxyphosphonoacetic acid or a salt thereof is present in said medium.

4. The method according to claim 1, wherein the medium contains scale-forming calcium and/or magnesium ions and the medium and metal surfaces are those contained in a cooling system, a steam generating system, a saline evaporator, a hydrostatic cooker, a gas scrubbing system or a closed circuit heating system.

5. The method according to claim 1, wherein the 2-hydroxyphosphonoacetic acid or salt thereof is present in conjunction with one or more of a further corrosion inhibitor, a dispersing or threshold agent, a precipitating agent, an oxygen scavenger, a sequestering agent, an antifoaming agent or a biocide.

6. The method according to claim 5 wherein the further corrosion inhibitor is triethanolamine.

7. The method according to claim 6 wherein triethanolamine is present in an amount such that the ratio of 2-hydroxyphosphonoacetic acid triethanolamine is from 2:1 to 1:20.

* * * * *